!

US007923228B2

(12) United States Patent
Nonomura

(10) Patent No.: US 7,923,228 B2
(45) Date of Patent: Apr. 12, 2011

(54) **METHODS AND COMPOSITIONS FOR GROWTH OF HYDROCARBONS IN *BOTRYOCOCCUS* SP**

(76) Inventor: Arthur M. Nonomura, Litchfield Park, AZ (US)

( * ) Notice: Subject to any disclaimer, the term of this patent is extended or adjusted under 35 U.S.C. 154(b) by 838 days.

(21) Appl. No.: 11/429,536

(22) Filed: May 5, 2006

(65) Prior Publication Data

US 2006/0252138 A1    Nov. 9, 2006

Related U.S. Application Data

(60) Provisional application No. 60/678,711, filed on May 6, 2005.

(51) Int. Cl.
*C12P 5/00* (2006.01)
(52) U.S. Cl. ............. 435/166; 435/257.2; 435/410; 435/431
(58) Field of Classification Search ............ 435/166
See application file for complete search history.

(56) References Cited

U.S. PATENT DOCUMENTS

| 4,383,039 | A | 5/1983 | Leavitt | 435/107 |
|---|---|---|---|---|
| PP6,169 | P | 5/1988 | Nonomura | |
| 5,476,787 | A | 12/1995 | Yokoyama et al. | 435/262.5 |
| 2006/0252138 | A1 | 11/2006 | Nonomura | 435/166 |
| 2006/0265800 | P1 | 11/2006 | Nonomura | |

FOREIGN PATENT DOCUMENTS

WO          2006/121950          11/2006

OTHER PUBLICATIONS

Dayananda et al., Effect of media and culture conditions of growth of hydrocarbon production by *Botryococcus braunii*, Process Biochemistry, 2005, vol. 40, p. 3125-3131.*
http://www.maximumyield.com/article 235 htm (2003).
Jian Qin et al; "Bio-Hydrocarbons from Algae"; Australian Government Rural Industries Research and Development Corporation, Feb. 2005.
S.J. Lee et al.; "Effects of harvesting method and growth stage on the flocculation of the green alga *Botryococcus braunii*"; Letters in Applied Microbiology, vol. 27, 1998 pp. 14-18.
P.Metzger et al.; "*Botryococcus braunii*: a rich source for hydrocarbons and related ether lipids"; Appl. Microb. Biotechnol, vol. 66, 2005 (published online 2004).
R.C. Hochmuth et al; "Hydroponic Nutrient Effluent—A Recoverable Energy Resource", University of Florida Cooperative Extension Service, Apr. 1999 p. 1-4.
A.Torres et al; Characterization of surface n-alkanes and fatty acids of the epiphytic lichen *Xanthoria parietina*, its photobiont a green alga *Trebouxia* sp., and its mycobiont, from the Jerusalem Hills, Eur. J. of Biochem, vol. 270, 2003, pp. 2120-2121 especially.
The International Search Report dated Oct. 2, 2006.
Office action dated Mar. 30, 2009 and Notice of Allowance dated Jun. 11, 2009 (in co pending U.S. Appl. No. 11/429,531).
Chu, S. P. 1942. J. Ecol. 30: pp. 284-325; "The Influence of the Mineral Composition of the Medium on the Growth of Planktonic Algae".
Phytochemistry, vol. 28, No. 11, pp. 3043-3046, 1989; Zheng Huang et al.; "Isoshowacene, AC31 Hydrocarbon From *Botryococcus braunii* Var. Show A".
J.Org. Chem. 1988, 53, 5390-5392; Zheng Huang et al.; "Isobraunicene, Wolficene, and Isowolficene. New Cyclic 1'-3 Fused Isoprenoids from *Botryococcus braunii*".
J.Org. Chem. 1988, 53, 4089-4094; Zheng Huang et al.; "Braunicense. Absolute Stereochemistry of the Cyclohexane Ring".
J.Am.Chem.Soc. 1988, 110, pp. 3959-3964; "Braunicene, a Novel Cyclic C32 Isoprenoid from *Botryococcus braunii*".
Food and Feed Crops of the United States, Second Edition, Revised; GM Markle, et al., 1998.
Index of Garden Plants; The New Royal Horticultural Society Dictionary; Mark Griffiths, 1994.
Center for Phycological Documentation; Index Nominum Algarum, 2005.
Jpn. J. Phycol. (Sorui) 36: 285-291, Dec. 10, 1998; Arthur Michio Nonomura; *Botryococcus braunii* var. showa (Chlorophyceae) from Berkeley, California, United States of America.
Arch Microbiol (1984) 140: 101-106; Masayuki Ohmori et al.; "*Botryococcus braunii* carbon/nitrogen metabolism as affected by ammonia addition".
J. Phycol. 21, 388-396 (1985); Fred R .Wolf et al.; "Growth and Branched Hydrocarbon Production in a Strain of *Botryococcus braunii* (Chlorophyta)".
Western Fertilizer Handbook, 1985.
Office Action dated Apr. 1, 2008 (in co-pending U.S. Appl. No. 11/429,531).
Office Action dated Sep. 5, 2008 (in co-pending U.S. Appl. No. 11/429,531).

* cited by examiner

*Primary Examiner* — Jon P Weber
*Assistant Examiner* — Tiffany M Gough
(74) *Attorney, Agent, or Firm* — Nields, Lemack & Frame, LLC

(57) ABSTRACT

Acceleration of botryococcenoids and growth by concomitant provision of appropriate light, minerals, and assimilable carbon. Specifically, methods, compositions and systems for the in vitro growth of hydrocarbons in photosynthetic organisms while maintaining a biologically exclusive monocultural environment, as for example, from *Botryococcus* species, is disclosed. Niche-nutrients can include about 200 ppm to about 3% nitrogen, and about 100 ppm to about 15% $P_2O_5$, and about 100 ppm to about 3.5% $K_2O$. In certain embodiments, the present invention relates to the growth of the Chlorophyta such as *Botryococcus* sp. in a nutrient medium that includes up to 15% phosphates, at least 3 ppm soluble iron, and up to about 70 ppm soluble zinc. Also disclosed is a substantially pure culture of *Botryococcus braunii* var. Showa, strain Ninsei, having the ATCC Accession No. PTA-7441, its parts, and hydrocarbons produced therefrom.

22 Claims, 4 Drawing Sheets

Schematic for hydrocarbon production from *Botryococcus* sp.

METHODS AND COMPOSITIONS FOR GROWTH OF HYDROCARBONS IN *BOTRYOCOCCUS* SP

CROSS-REFERENCE TO RELATED APPLICATIONS

This application claims priority of provisional application Ser. No. 60/678,711, filed May 6, 2005, the disclosure of which is hereby incorporated by reference. This application is related to co-pending plant patent application entitled THE NINSEI VARIETY OF *BOTRYOCOCCUS*, filed May 5, 2006 Ser. No. 11/429,531, the disclosure of which is hereby incorporated by reference.

BACKGROUND OF THE INVENTION

The present invention is a novel and distinct process for commercial growth of hydrocarbons in photosynthetic organisms while maintaining a biologically exclusive monocultural environment, as for example, in the case of the present invention, from *Chlorophyta, Trebouxiophyceae*, and particularly *Botryococcus* species.

For decades, *Botryococcus* species have been suggested as potential sources of liquid transport fuels (Wolf, et al. 1985). Academically, *Botryococcus* species have proven quite attractive for their natural chemistries, but the cost for production of a gallon of renewable transport fuel exceeded the sales price of fossil fuels. A number of different culture conditions have been investigated, but a defined system for competitive growth of transport fuels has not been disclosed previously. Humanity would benefit from development of a reliable system for production of petroleum-type hydrocarbons from a renewable energy source.

*Botryococcus* is a primitive colonial photosynthetic organism, dating from 300 million years ago, and may be regarded as a living fossil; as, indeed, *B. balkachicus; B. coorongianus; B. luteus*; and *B. palanaensis*, are true fossil deposits. Oil shale is populated with botryococcite fossils from which petroleum deposits arose. Shale originates from mud, and in consideration of the fossil record, the methods, compositions and organisms of the present invention, allow for expression of the mud origins of live *Botryococcus* species, including the following: *B. australis, B. braunii, B. braunii* var. *horridus, B. braunii* var. *minor, B. braunii* var. *perarmatus, B. braunii* var. *Showa, B. braunii* var. *validus, B. calcareous, B. canadensis, B. comperei, B. fernandoi, B. giganteus, B. micromorus, B. neglectus*, and *B. pila*. As a result of defining its proper niche in the course of the present invention, rapid growth at the water-to-air interface was made possible by elimination of biological competition.

At the surface of mud, water evaporates and salts become concentrated to the extent that crystals may accumulate at the surface. In the present invention, I have discovered that, consistent with a mud niche, a flotation mechanism related to hydrocarbon metabolism may have evolved in photosynthetic organisms to utilize the concentrated nutrient salts at moist surfaces. That is, through natural selection, *Botryococcus* sp. became one of the most successful photosynthetic eukaryotes on Earth by survival in an environment intolerable to competitors. In the present invention, the environmental tolerances that made *Botryococcus* sp. the fittest for hundreds of millions of years are defined and utilized in novel systems for growing hydrocarbons such as gasoline commercially. Based on this understanding of Darwin's concept of, "survival of the fittest," oleomic photosynthetic organisms were tested in nutrient salts at very high concentrations. Surprisingly, *Botryococcus* sp. thrived in hundreds times the concentrations of the salts in conventional nutrients. The present invention exploits the aforementioned discovery of the exclusive niche of *Botryococcus* sp.

SUMMARY OF THE INVENTION

The present invention relates to methods, compositions and systems for the in vitro growth of hydrocarbons in photosynthetic organisms while maintaining a biologically exclusive monocultural environment, as for example, from *Botryococcus* species. The environmental tolerances that made *Botryococcus* sp. the fittest for hundreds of millions of years are defined and utilized in novel systems for growing gasoline on a commercial scale. The present inventor discovered that *Botryococcus* sp. thrived in many times the concentrations of the salts in conventional nutrients; it out-competes all other life forms by living in a chemically extreme environment of high concentrations of all of its nutrient chemicals. The present invention exploits the aforementioned discovery of the exclusive niche of *Botryococcus* sp.

In certain embodiments, niche-nutrients include about 200 ppm to about 3% nitrogen, and about 100 ppm to about 15% $P_2O_5$, and about 100 ppm to about 3.5% $K_2O$. In certain embodiments, the nutrient medium is a balanced nutrient salt formulary comprising phosphate salts and including ammonium salts, calcium salts, potassium salts, magnesium salts, sodium salts, phosphoric acid, pyrophosphates, polyphosphates, glycerophosphates, and the like; with soluble potassium phosphates, most highly preferred.

In certain embodiments, the present invention relates to the growth of the Chlorophyta such as *Botryococcus* sp. in a nutrient medium that includes about 800 ppm to 15% (150,000 ppm) phosphates and about 2 ppm to about 70 ppm soluble zinc.

In certain embodiments, the present invention relates to the growth of photosynthetic organisms such as *Botryococcus* sp. in a nutrient medium that includes soluble iron, manganese and magnesium at concentrations far greater than conventional phycological nutrients in order to further enhance synthesis of hydrocarbons.

In certain embodiments, the present invention relates to the growth of the Chlorophyta such as *Botryococcus* sp. in a nutrient medium that includes phosphate salts, including, ammonium salts, calcium salts, potassium salts, magnesium salts, sodium salts, phosphoric acid, pyrophosphates, polyphosphates, glycerophosphates, and the like, phosphate buffers comprised of monobasic, dibasic, and tribasic salts; citrates; Krebs Cycle carboxylates; and derivatives thereof and the like. Suitable ranges of nutrients include 0.800 ppm to 30% phosphates, with preferred phosphate concentration of from about 0.800 ppm to about 3% phosphates, about 25 ppm to about 250 ppm soluble magnesium, about 0.3 ppm to about 3 ppm soluble manganese, about 0.3 ppm to about 10 ppm soluble iron, preferably about 5 ppm to about 9 ppm soluble iron, most preferably about 6 ppm to 8 ppm soluble iron, and about 0.2 ppm to about 70 ppm soluble zinc ($Zn^{+2}$).

In certain embodiments, the present invention relates to a method for the production of hydrocarbons which comprises cultivating species of the Chlorophyta in a nutrient medium having a phosphate content of at least about 2 mM, a zinc content of at least about 0.2 ppm, and an iron content of at least about 3 ppm, harvesting the cultivated strain, and recovering therefrom said hydrocarbons, wherein the cultivating step produces a biomass, and further comprising exposing the Chlorophyta to a second nutrient medium having a phosphate content of at least about 80 mM.

In certain embodiments, the nutrient medium further comprises 200 ppm to 30,000 ppm N, 100 ppm to 150,000 ppm $P_2O_5$, and 100 ppm to 35000 ppm $K_2O$.

The present invention also relates to a substantially pure culture of *Botryococcus braunii* var. Showa, strain Ninsei, having the ATCC Accession No. PTA-7441, its parts, and hydrocarbons produced therefrom.

DETAILED DESCRIPTION OF THE INVENTION

Assay

Figure 1:
FIG. 1 shows the meniscus at the top of a clear glass culture cylinder that is highly populated with colonies of *Botryococcus* sp. afloat at the surface and in the thin film of water being drawn above the meniscus by capillary action of the mass aggregate of colonies. The culture was lightly tapped just prior to photography to release some colonies into the water below the meniscus to display separated colonies as best as possible, and, as a result, the colonies followed a sine wave pattern into submergence just below the surface. All colonies that were submerged by the wave, floated back again to the meniscus. The unit of scale to the right is in millimeters. The colonies can be cultured on any water-moistened solid surface that can hold and supply nutrients in an aqueous medium, including, paper, plastic, colloids, phycocolloids, agar, agarose, carrageenan, agar substitutes, textiles, gel, mud, soil, earth, shale, clays, foam, ceramics, concrete, brick, metal foam, wovens, nonwovens, and solid and liquid substrates of all types.
Figure 2:
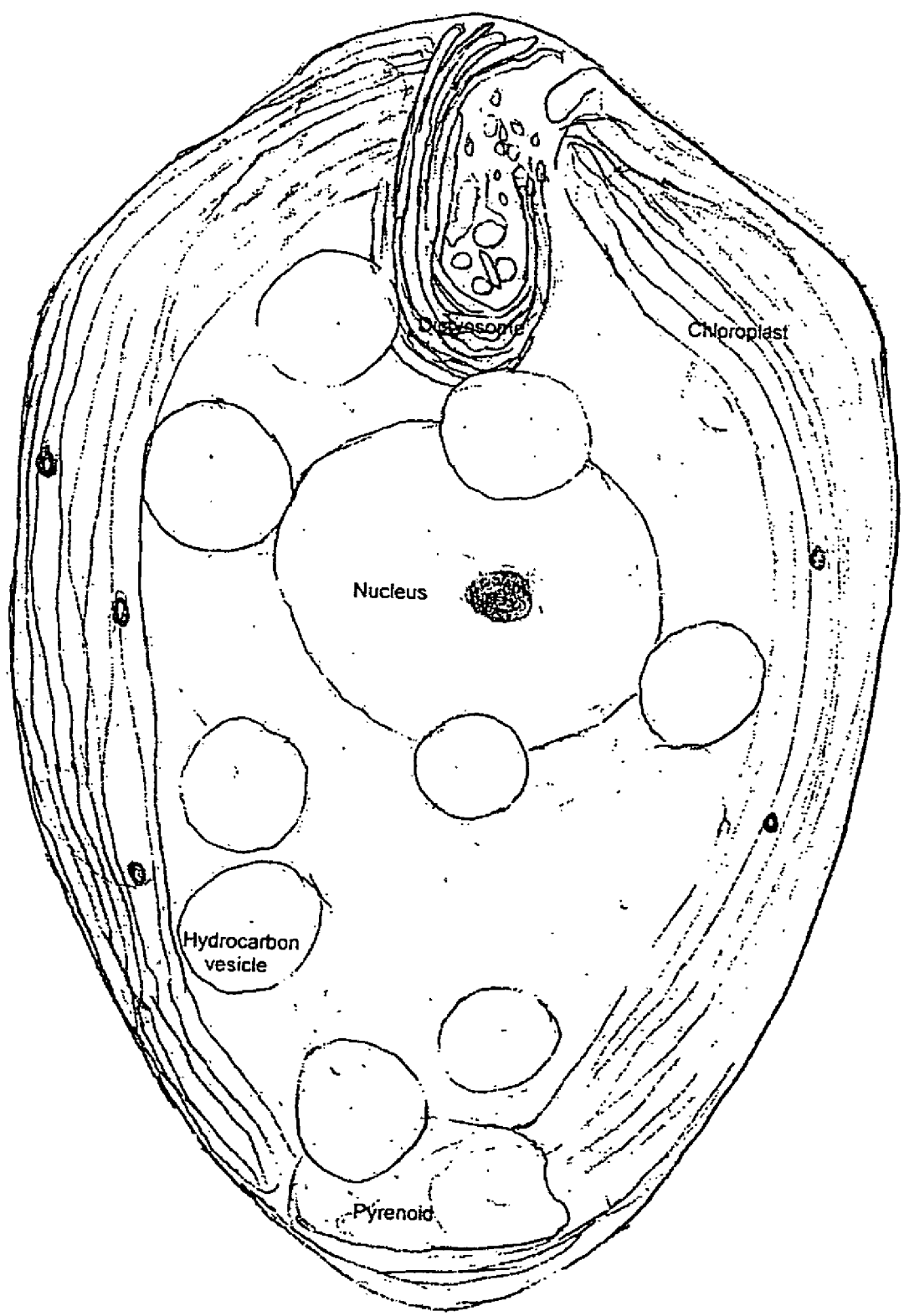
FIG. 2 illustrates a 5 µm breadth by 8 µm height cell of a colony showing an ovoid cell containing nine round hydrocarbon vesicles, a dictyosome, a nucleolus, and a parietal chloroplast.

Previous investigations (Ohmori, et al. 1984; and Wolf, et al, 1985) verified that colonies containing greater than 20% of dry weight as botryococcenoid hydrocarbons were buoyant and that colonies containing less than 5% hydrocarbons remained sunken at the bottom of the culture vessel, providing a visual method for selecting cells with commercial-grade hydrocarbons. FIG. 1 shows floating colonies of *Botryococcus* sp. with a corresponding 30% hydrocarbon content. Additionally, the hydrocarbon-vesicle counts within cells, as drawn in FIG. 2, were found to be in direct correlation to hydrocarbon yields, providing microscopy for confirming selection of cells and colonies with high hydrocarbon contents. Colonies in hydrocarbon-enhancement were placed in the dark without supplemental carbon dioxide gas to eliminate artifacts of flotation from bubbles. Environmental conditions were 150 µE/m²/sec PAR to 1700 µE/m²/sec PAR at 25-37° Centigrade. Nutrient chemicals were reagent grade in all laboratory-scale experiments. In field-scale tests, fertilizer grade chemical nutrients were provided. In order to minimize or eliminate ammonia, nitrates were optionally kiln dried prior to admixture. Supplementation with 0.1% to 100% carbon dioxide gas or carbonate (e.g., 10 mg/ml sodium bicarbonate or potassium bicarbonate) increased hydrocarbon synthesis substantially, especially, when under the highest light intensities with soluble elements of the present invention.

Clones of *Botryococcus* sp. originated from the collections from Nature. Axenic clones, from the Ninsei strain disclosed in provisional application Ser. No. 60/678,711, filed May 6, 2005 and incorporated herein by reference, micropropagated rapidly in light on novel carbon- and nutrient-supplemented solid media. Solids included selections from 0.5% to 1.5% agar, colloids, gelatin, plastic gels, cellulose, plant fibers, synthetic fibers, polymers, woven fabrics, nonwovens, paper, broadcloth, iron, stainless steel, netting, moist glass, brick, concrete, plastic, foams, nylon, and ceramic surfaces. Sunken colonies with very low hydrocarbon content were archived as controls in Showa nutrients, U.S. Patent Plant 6169, and are incorporated by reference herein, to provide controls in experiments. Up to the point of experimentation, the varieties were variously maintained in Showa media; Chu 13 (Chu 1942); other conventional phycological nutrient media; and were supplemented with trace minerals, spring water, or soil-water extracts in aqueous solution. *Botryococcus* sp. was maintained in defined iron-, zinc- and phosphate-enriched media of the present invention.

Colonies of Ninsei are variably-shaped groups of cells held together in the cups of tough sporopollenin-like matrices. Depth of color depends on the light regime, density or culture and physiological state of the colonies. All color designations are made with reference to the Munsell Book of Color. Normal healthy colonies range from 5 GY 7/8 to 2.5 GY 8/12 on the Munsell color chart and these Ninsei colonies, fully pigmented with chlorophylls, may float at the surface of growing cultures with high hydrocarbon content that may reflect golden overtones.

The Ninsei variety is characterized at an average green hue of 2.5 GY 6/10±50% on the Munsell color chart for healthy colonies. In contrast, Showa is described as a yellow of 2.5 Y 7/8 on the Munsell color chart. Vegetative reproduction resulting in increased colony count is maintained as long as there is chlorophyll content to reflect 2.5 GY hues. No growth has been observed in the Y through YR Munsell Color range, but conversion of carbon stores to hydrocarbon may continue up into the YR brown state of decline. Flotation is concomitant with growth of botryococcenes branched hydrocarbons ($C_nH_{2n-10}$, n=30-37). When released from the colonial matrix, cells of the colonies are 5 µm to 10 µm spheres often pressed by neighboring cells into irregular shapes. Within the colony, the cells are wedged into an almond-shape between neighboring cells. Deposits of hydrocarbon, 0.1 µm to 1 µm in diameter, are present in the cytoplasm, wall, and matrix. An occasional cell of Ninsei exhibits a depression at the outer tip of the cell that most frequently appears in cells with few hydrocarbon vesicles and may be a result of secretion of oils. The name of the strain is, in fact, derived from the urn shape of cells, reminiscent of shapes of large ceramic wares by the artist of Kyoto, ca. 1600 AD, Ninsei.

The colonial unit is spherical and aggregates of units contribute to the formation of irregular grape-like clusters observed in large colonies. During rapid growth of the novel strain, colonies are generally smaller than Showa's 50 µm colonies. In Ninsei, smaller colonies may range from 10 µm to 45 µm in diameter. Colonies of 100 or more cells are predominantly composed of irregularly shaped units that fragment into roughly rounded colonies. Ninsei is visually distinguishable from other strains of the variety by its deep green hue, small size attributable to rapid growth, cell structure, and niche. *Botryococcus braunii* var. Showa, strain Ninsei was deposited at the American Type Culture Collection (Post Office Box 1549, Manassas, Va. 20108) in March 2006 and assigned ATCC No. PTA-7441.

Solution culture nutrient concentrations meant for vascular plant crops, widely recognized by crop nutritionists for the past half century as defined hydroponic fertilizer formulae for flowering plants, had not been previously applied to *Botryococcus* species. Generally, hydroponic culture media effectively suppress protistans by being far too highly concentrated for unicellular organisms. In contrast, for the present invention, *Botryococcus* species were found to grow in full-strength Hydroponic Solutions and, to the complete surprise of the inventor, in nutrient salt concentrations previously thought to be toxic to plants and to other life. For the present invention, major modifications were made to substantially increase zinc, potassium, calcium, magnesium, manganese, iron, and phosphate concentrations well beyond those of the conventional phycological and hydroponic solutions. Phosphate salts provided the additional benefit of buffering within a range of pH 6 to pH 7. Furthermore, concentrations of soluble zinc ions ($Zn^{+2}$) were increased one hundred times to two thousand times that of final concentrations found for soluble zinc in vegetable crop production; and soluble iron was increased up to quadruple the concentration used in vegetable solution culture. For example, in hydroponics the following final concentrations of nutrient elements has been widely regarded by those in the field for the successful solution culture of tomato crops: "119 ppm N; 30 ppm P; 140 ppm K; 100 ppm Ca; 24 ppm Mg; 32 ppm S; 2.5 ppm Fe; 0.25 ppm B; 0.25 ppm Mn; 0.025 ppm Zn; 0.01 ppm Cu; and 0.005 ppm Mo," (Growing Plants in Solution Culture, in Hawkes, G. R. et al, editors, (1980), *Western Fertilizer Handbook*, The Interstate Printers and Publishers, Inc., Danville, Ill. Pages 185-193).

The preferred nutrient enrichment solution of the present invention is hereinafter denoted as KwiK (see Table below). *Botryococcus* sp. was rapidly propagated in KwiK and it should be noted that the preferred mild formulation of KwiK contains over fifty times the total phosphates and many times higher $Zn^{+2}$ concentrations than Chu 13 (Table Comparing Media, below) and hydroponic media.

The present invention comprises trials with Trebouxiophyceaen *Botryococcus* species; hereinafter *Botryococcus* sp. The preferred environment for maintenance of colonies required buffering by appropriate concentrations of nutrient phosphate salts and carbonate adjusted to pH 6.3 to pH 6.8, preferably to pH 6.7. Colonies of *Botryococcus* sp. floated within hours when supported by the ZiP medium of the present invention, containing 80 mM to 150 mM total phosphates and up to 70 ppm $Zn^{+2}$, in a range between pH 7.0 to pH 8.3, and under high light intensity, and it was, thereupon, hypothesized that the organism prefers the surface niche where moisture, illumination, and high salt concentrations abound.

EXPERIMENTAL

Methods, compositions and systems of the present invention provide means for in vitro growth of transport fuel hydrocarbons.

Stock cultures were taken from bottom-dwelling colonies that had been maintained in conventional liquid culture media, typified by approximately 1 ppm to 10 ppm phosphate, 0.01 ppm to 0.3 ppm iron, and 0.01 ppm to 0.5 ppm zinc, as for example, in Showa medium and other phycological media. Aqueous nutrient solutions were placed in sterile culture tubes and flasks and steam sterilized twice for 60 minutes. Following inoculation and growth, colonies were concentrated with overnight settling and approximately one million submerged green colonies were collected from the bottom of culture vessels. Equal volumes were resuspended into replicate culture vessels with equal volumes of enhancement media in the highest light intensities available in preparation for experiments. Control cultures were transferred into equal volumes of Showa medium and placed side by side under identical conditions as controls.

In water with up to 300 mM phosphates, bottom-dwelling colonies began to rise to the surface within 5 hours. After two weeks or more in 300 mM phosphate, the colonies remained floating, but cleared to amber. By analysis of a subtractive matrix, eliminating individual compounds from each application, greater than 80 mM total phosphates, hundreds of times the concentration of phosphate salts of conventional phycological media, stimulated the rise of colonies to the surface, most rapidly when in the presence of soluble ions of Mg, Mn, Fe, and $Zn^{+2}$. The same buoyant response of all of the colonies occurred in the presence of correspondingly high concentrations of balanced equimolar phosphate salts, regardless of the counter-ions whether they were selected from ammonium, potassium, magnesium, or sodium. It was also important to balance acidic with basic phosphate salts at equimolar concentrations because a 2 mM difference was found to exceed the pH-tolerance of phycological specimens.

With further testing and modifications of the highly concentrated salts to reflect nitrogen-phosphoric-potash, N—P—K, typical of hydroponic nutrients, and with chelated secondary and trace minerals, the preferred buffered enrichment solution with 80 mM to 120 mM potassium phosphate was developed for the present invention. The solution was adjusted to fall within a range of about pH 6.5 to pH 7 by regulation of approximately equimolar mono- and di-potassium phosphates (MKP and DKP) or other phosphate salts. Phosphates were selected because of the high-energy requirement of adenosine triphosphate, ATP, for metabolism of cellular resources into hydrocarbons. Potassium was selected as the counter-ion of choice because it is a major nutrient that does not precipitate at high concentrations. In the present invention, supplementation with 1 ppm to 90 ppm soluble $Zn^{+2}$ was critical to acceleration of hydrocarbon chain elongation and 0.1 ppm to 10 ppm soluble iron was essential to photosynthesis. That is, in illuminated cultures in KwiK supplemented preferably with 5 ppm soluble zinc and iron, colonies grew hydrocarbons at an accelerated rate by provision of a controlled upwelling of Kwik power. Therefore, trace minerals were modified by replacing the mineral salts with chelated salts at 0.03 ppm to 50 ppm concentrations for each element in order to maintain solubility in the presence of high concentrations of phosphate. In the course of the present invention, rapid hydrocarbon production by green colonies was maintained in the presence of KwiK elements with the most highly preferred concentration of 5 ppm to 9 ppm soluble iron. Enrichment by $Zn^{+2}$ and phosphate in a second nutrient solution was found to enhance hydrocarbon content of the colonies while providing a biologically competitive advantage to the colonies of the present invention. The enriched solution for accelerated hydrocarbon production is, hereinafter, denoted ZiP. In the process development of *Botryococcus* sp., colonies from populations floating above the meniscus of ZiP were visually verified with high hydrocarbon-vesicle counts, harvested and transferred to ZiP to ripen with hydrocarbons.

Maintenance of cultures for long durations under high light intensity illumination ranging from 500 to 1700 μE/m$^2$/sec PAR, 8-20 h light, at 25-35° C. is preferred in KwiK supplemented with saturated carbon dioxide or bicarbonate, especially when under the highest light intensities. Alternatively, carbonated water with ZiP may be metered in to maintain rapidly growing hydrocarbons. The buoyant colonies of the present invention were characterized by high growth content, upwards of 5% to 50% dry weight of mixed lipids. The preferred environment for maintenance of the floating colonies requires buffering by appropriate concentrations of available 20 mM to 125 mM phosphates, 3 ppm to 10 ppm Fe, and 0.1 ppm to 70 ppm $Zn^{+2}$, where 80 mM to 90 mM phosphates with 0.2 ppm to 45 ppm chelated $Zn^{+2}$ is preferred. Colonies tolerate a broad physiological range from pH 5.5 up to pH 8.3; however, under high light intensity and with carbonate availability, continuous adjustment to maintain pH 6.8 is essential to maintain the solubility of minerals in high concentrations of phosphate. Organic substrates for enhancement of hydrocarbons include 1 mm to 100 mM Krebs Cycle carboxylates, preferably with citrate as an acid component of citrate-phosphate buffer; mevalonates; methionines, preferably adenosyl-methionine; alcohols; and fatty acids. For rapid growth, at concentrations above 1 mM total phosphates, it is important to prevent precipitation, especially by calcium and magnesium, by addition of appropriate concentrations of sequestering agents such as disodium-, diammonium-, and dipotassium-ethylenediaminetetraacetates; citrate; carboxylates; and the like. Additionally, maintenance of acidic environments assists with solubility of media with high concentrations of phosphate. Agriculturally accepted sources of $Zn^{+2}$ include, without exclusion of any other zinc salts, zinc sulfate, zinc oxide, zinc carbonate, zinc chloride, zinc citrate, zinc oxysulfate, zinc ammonium sulfate, and zinc nitrate, supplemented by chelation with, for example, salts of EDTA, HEEDTA, NTA, DTPA, EDDHA, and the like. Commercially available 6% to 14% $Zn^{+2}$ as diammonium EDTA may be alkaline which may be compensated by addition of the monobasic phosphate salt to adjust the final solution to pH 7. Sources of iron include, without exclusion of any other iron supplements, iron sulfate, iron oxide, iron filings, ferric chloride, ferric ammonium citrates, ferrous salts, soil extracts, and supplemented by chelation with, for example, salts of EDTA, HEEDTA, NTA, DTPA, EDDHA, and the like. The most highly preferred medium eliminates all sources of ammoniacal nitrogen in order to fully enhance hydrocarbon production of mass cultures. It is the hypothesis of the present invention that hydrocarbon synthesis may be fully optimized by providing nutrients beneficial to photosynthesis, including 50 ppm to 200 ppm magnesium as part of the chlorophyll molecule and about 5 ppm to 10 ppm soluble iron that is essential to electron transport. Preferably, in for example KwiK or ZiP, inclusion of 7 ppm to 9 ppm soluble ferric or ferrous ions in the media accomplishes the same when balanced equally by 0.2 ppm soluble Mn, and with provision of high light intensity illumination, carbon dioxide gas, and 0.2 ppm to 50 ppm $Zn^{+2}$, the synthesis of hydrocarbons may be optimized.

For a population of *Botryococcus* colonies, 2 mM (348 ppm) and greater concentrations of phosphates, 500 ppm to 1200 ppm nitrate salt, 500 ppm potassium salt, 3 ppm to 10 ppm Fe, 0.1 ppm to 3 ppm Mn, and 0.1 ppm to 5 ppm $Zn^{+2}$ are required for long-term growth of hydrocarbons. The recommended and preferred upper limits are 120 mM total phosphates at pH 7 and 50 ppm soluble zinc. For hydrocarbon synthesis, supplementations with 25 ppm to 250 ppm soluble magnesium, 0.2 ppm soluble manganese, 5-9 ppm soluble iron, and 0.1 ppm to 50 ppm $Zn^{+2}$, are preferred. Trace metals are preferably chelated. Most preferably, for maintenance of the growth of hydrocarbons, the medium is supplemented as specified in KwiK. The preferred method for making ZiP is to mix and sterilize a solution of 160 mM to 400 mM total phosphates and add equal volumes of the phosphate solution to pre-sterilized KwiK resulting in 80 mM to 200 mM total phosphates ZiP solutions with chelated nutrients. The preferred ZiP solution at 88 mM to 150 mM balanced phosphates with 2 ppm to 50 ppm $Zn^{+2}$ and with 10 ppm to 20 ppm Fe in KwiK supports growth of hydrocarbons.

The biosynthesis of hydrocarbons is an energy-intensive pathway that may be accelerated by the availability of very high concentrations of ferrous, ferric, $Zn^{+2}$ and phosphates of the present invention. Thus, the enzymes in this system require phosphate-energy-complexes, such as the $Zn^{+2}$-requiring farnesyl pyrophosphate synthase, as demonstrated in the current invention. As the photosynthetic organism also responds rapidly to the uppermost concentrations of phosphates, commercial batch-processing of colonies is envisioned, whilst continuous processing of partial populations in KwiK is an open option. Notably, exposure to 200 mM to 300 mM phosphates and to 100 ppm $Zn^{+2}$ resulted in a color change of the colonies toward amber over the long duration of approximately two to eight weeks, implicating rapid batch processing as the method of choice.

KwiK Medium, Adjusted to pH 7 with Phosphate Buffer

| KwiK Component | Concentration | |
|---|---|---|
| | Range | Preferred |
| $KH_2PO_4$ | 80-800 ppm | 136 ppm |
| $K_2HPO_4$ | 80-1000 ppm | 174 ppm |
| $KNO_3$ | 500-2500 ppm | 570 ppm |
| Chelants | 80-1500 ppm | 200-1000 ppm |
| $MgSO_4$ | 1-1000 ppm | 100 ppm |
| $Ca^{+2}$ | 1-800 ppm | 88 ppm |
| Fe | 0.3-20 ppm | 5 ppm to 10 ppm |
| Mn | 0.1-3 ppm | 0.2 ppm |
| Cu | 0.01-0.1 ppm | 0.01 ppm |
| B | 0.2-2 ppm | 0.2 ppm |
| $Zn^{+2}$ | 0.3-50 ppm | 2 ppm |
| Mo | 0.001-0.05 ppm | 0.02 ppm |
| Co | 0.001-0.05 ppm | 0.002 ppm |

ZiP Medium, Adjusted to pH 7 with Phosphate Buffers

| Zip Component | Concentration | |
|---|---|---|
| | Range | Preferred |
| Phosphates | 0.1% to 3% | 0.5% to 0.8% |
| $Zn^{+2}$ | 0.2 ppm to 70 ppm | 36 ppm to 50 ppm |

Organic ZiP Medium in Spring Water

| ZiP Component Supplement | Concentration | |
|---|---|---|
| | Range | Preferred |
| Citrate-Phosphate Buffer | 0.1% to 3% | 0.8% to 2% |
| $Zn^{+2}$ | 0.2 ppm to 70 ppm | 36 ppm to 50 ppm |
| Potassium acetate | 0.1% to 3% | 0.5% to 1% |

| Comparisons of Nutrient Media | | | |
|---|---|---|---|
| Nutrient Salt | KwiK | ZiP | Chu 13 |
| $KH_2PO_4$ | 272 ppm | 1.4% | 0 |
| $K_2HPO_4$ | 348 ppm | 1.7% | 0.001% |
| $KNO_3$ | 570 ppm | 0.05% | 0.005% |
| $Zn^{+2}$ | 2 ppm | 50 ppm | 0.5 ppm |

Colonies of *Botryococcus* sp. were found to live and grow at the surface of the water or on moist substrates, whereas, other general methods of culture involved immersion in water. Exceedingly slow growth has been observed in the Y through YR Munsell Color range and conversion of carbon stores to hydrocarbon may continue up into the amber state of decline without appropriate elements. Colonies of cells are held together by a matrix that is rich in hydrocarbons. As colonies accumulate hydrocarbons, they exhibit a correspondingly higher absorbance of ultraviolet light, as measured spectrophotometrically. This UV-absorbance characteristic of the present invention may be applied to cell-sorting instrumentation attuned to selection of colonies and cells with maximized hydrocarbon content. The colonial unit is spherical and aggregates of units contribute to the irregular grape-cluster formations observed in large colonies of the generic namesake from Latin, *Botryococcus*.

Colonies grow particularly well in KwiK-supplemented water-moistened solid media under continuous or periodic (e.g., 16:8 h LD) PAR light exposure, with high light intensities up to direct sunlight as high as 500 to 1700 µE/m²/sec in high density cultures and temperatures of 20° to 37°.

Defined growth media for the strains of the present invention include primary, secondary and trace metal plant nutrients. The most highly preferred formula provides balanced N—P—K at many times the concentrations of conventional nutrients. Balanced formulations include nitrate, phosphate and potash sources of fertilizers at rates exceeding hydroponics of flowering plants; as well as the secondary nutrients, $Ca^{+2}$, S, and Mg; and soluble micronutrients such as ions of Fe, Mn, $Zn^{+2}$, Cu, B, Mo, Co, and Ni. Through matrix analyses in the course of the present invention, it was found that supplementation with a cocktail of metal ions is preferred for maintenance of growth of hydrocarbons and preferably include 5 mM to 25 mM magnesium, 0.1 ppm to 3 ppm manganese, 3 ppm to 10 ppm iron, and 0.01 mM to 0.1 mM $Zn^{+2}$. Total phosphates may be in the range from 2 mM to 150 mM phosphates. Sources of typical solution culture nutrients are, for example, selected from myriad and various available compounds as generally accepted and known by those in the art.

The present invention elucidates the only process for which the growth of transport fuel hydrocarbons in *Botryococcus* may be undertaken by filling a chemical niche of KwiK and ZiP components. Such high Fe, $Zn^{+2}$ and phosphate concentrations have otherwise proven detrimental to lower photosynthetic organism as evidenced by the low concentrations of conventional formulations (as for example in Chu 1942; and US Patent Plant 6169). *Botryococcus* sp. produces chemical structures of $C_nH_{2n-10}$, n=30-37; $C_{25}$ to $C_{31}$ n-alkadienes and trienes; $C_{40}H_{78}$; carotenoids; and fatty acids; and isomers thereof.

*Botryococcus* sp. may have adapted to the chemical extremes of exclusive concentrations of phosphate, up to 3% in vitro, and as high as crystalline in Nature. Zinc and manganese have long histories of being formulated into human medications for their germ-fighting benefits and, thus, very high concentrations of Mn and $Zn+^2$ provide clear competitive advantages for *Botryococcus* sp. to survive where other microorganisms die. Flotation enables it to be transported to live at the surface or edge of the exclusive moist solid medium. *Botryococcus* sp. occupies the defined niche of the present invention. The preponderance of mixed hydrocarbons, when accumulated in high cellular concentrations, function as naturally effective ultraviolet sunlight blocking agents, necessary for survival on land; and as such, the whole organism as well as its extract may be utilized in topical sun block formulae.

Example 1

Hydrological shear forces are greatest at the air:water interface. When the liquid cultures of *Botryococcus* sp. in ZiP were placed in a shaker table (>100 rpm) cloaked in 3% carbon dioxide, oil was pressed out of the colonies by shearing forces. When brought to a stand still, the oil floated at the surface to be harvested by skimming.

In healthy sunlit water-borne cultures, colonies rose off the bottom to various levels up to the top half of the column in ZiP cultures supplemented with 36 ppm to 50 ppm $Zn^{+2}$, 120 mM phosphate and KwiK components at about pH 7. All control colonies in conventional phycological media dropped below the bottom half of the culture tube within an hour. After residing in the dark for 12 hours, colonies in ZiP remained floating at the meniscus, while, in contrast, the colonies of control cultures remained sunken at the bottom of the culture vessels. Starting from colonies maintained for a week in KwiK, the time to flotation of the population was approximately 1 day after exposure to ZiP. Rate of flotation was affected by species selection. Notably, the preferred formulation of ZiP contains over 300 times the phosphate and 100 times the zinc concentrations of Chu 13 (Table Comparing Media, above).

Example 2

Figure 3:
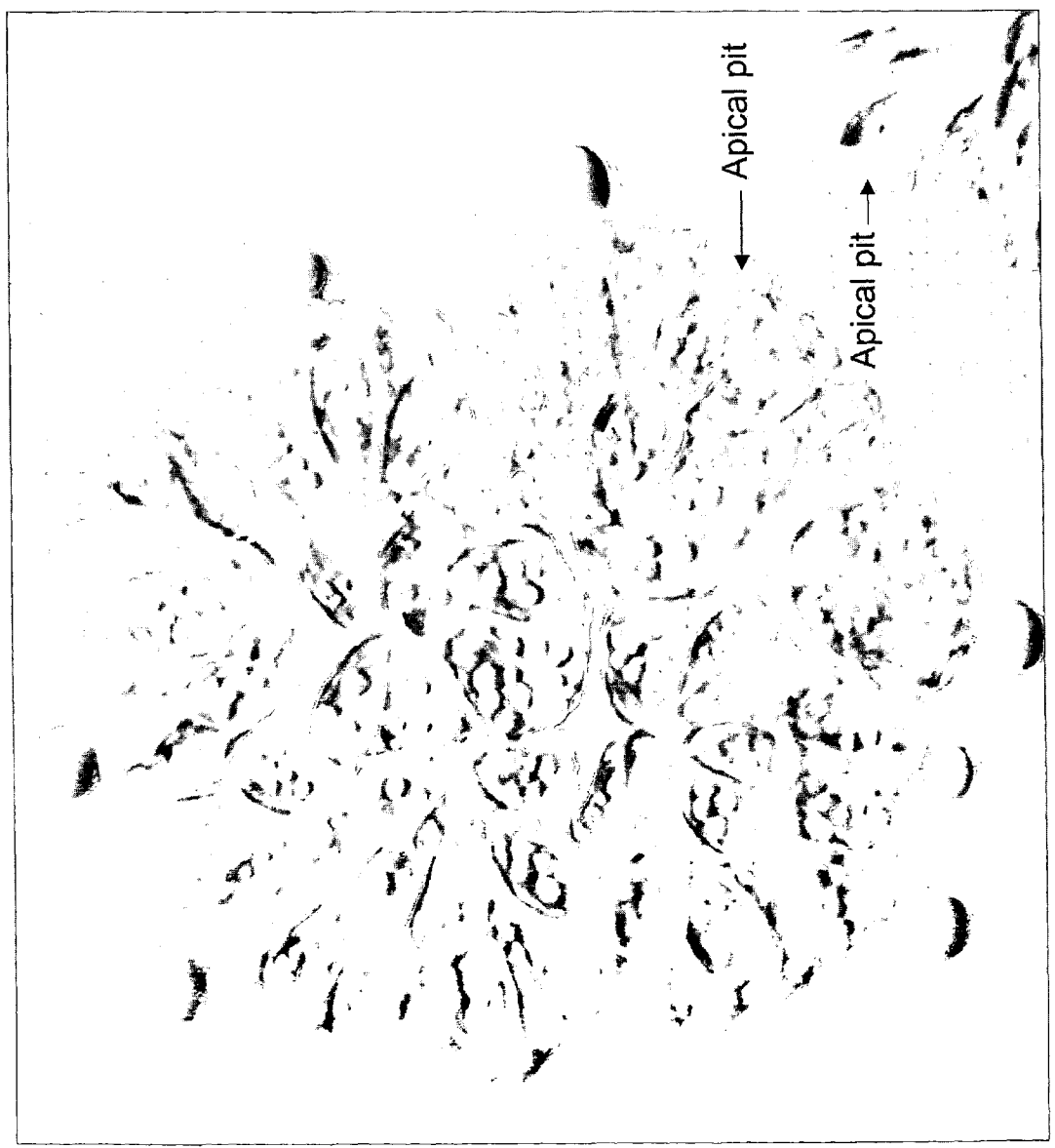
FIG. 3 is a microphotograph of a green hydrocarbon-rich colony showing ovoid protuberant cells, each containing five and more round hydrocarbon vesicles. At the perimeter are seven hydrocarbon droplets extruded from the colony by pressure from the glass cover slip.
Figure 4:
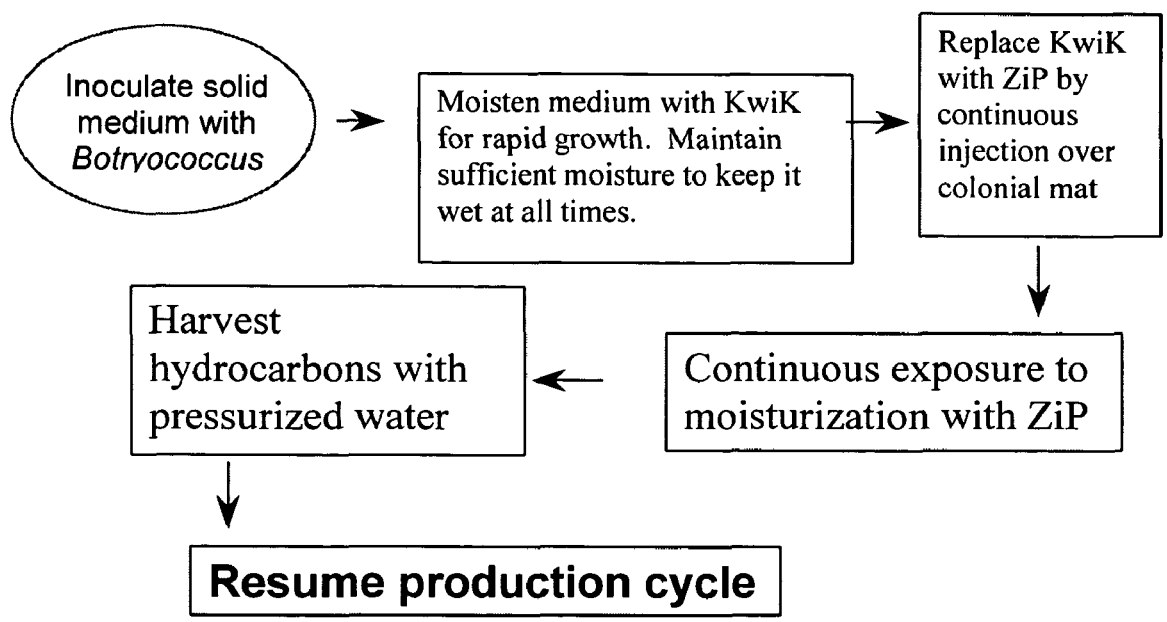
FIG. 4 is an exemplary schematic diagram of a hydrocarbon production process of the present invention.

The process system of the present invention is schematically depicted in FIG. 4, wherein the mud niche is mimicked by provision of a continuously moistened solid medium such as a fabric beltway that is sufficiently tight in its weave to prevent the colonies from slipping through. For example, 25 to 50 micron Nitex® Broadcloth is an appropriate selection. Nitex® Broadcloth 10 microns to 600 microns is the material of choice for plankton nets. The fabric belt is inoculated with *Botryococcus* spp. and growth is maintained by continuous misting with carbon dioxide gas-supplemented KwiK and natural solar illumination. Initially, gas-carbonation assists by sustaining acidity that prevents loss of metallic nutrients to precipitation. Different oleomic strains, varieties and species may be interspersed in the culture. When sufficient biomass is measured by achieving growth to 1 to 10 mm depth, the nutrient mist is replaced with a 10 mM bicarbonate-supplemented ZiP mist. Over time, bicarbonate raises the alkalinity of the nutrient solution, thus, provision of an oleomic environment is dependent upon metering appropriate buffering agents into the culture environment to maintain solubility of nutrients. The colonies are allowed sufficient time to ripen by visually monitoring hydrocarbon-vesicle counts within live cells taken through random samplings. At the determined time of maximum vesicle count exceeding 8 hydrocarbon-vesicles per cell in a given plane, as per FIG. 2, hydrocarbons are harvested from live cells by applying aqueous solutions or phytobland organic solvents as 30 PSI to 100 PSI pressurized misting sprays for 1 to 45 minutes. Applying pressure to exude hydrocarbons from cells was photographically recorded in FIG. 3, where exogenous droplets of oil droplets were visually observed in vivo. Preferably, pressurized water is applied to the mat following a design that supplies sufficient hydrological shear to press hydrocarbons out of the colonies while keeping the cells alive; therefore, the least pressure that forces exudation of oils is preferred and is dependent on the thickness of the mat. The cycle is repeated until the inoculum is exhausted.

The formulations and methods of the present invention may be applied to virtually any variety of living organism that metabolizes hydrocarbons, most preferably photosynthetic organisms. These photosynthetic organisms include protistans, bacteria, and plants. Plants include innumerable agricultural and horticultural species and varieties, known arts to those in the field.

The methods of the present invention are amenable to batch processing of captive hydrocarbon vesicles. Sheared botryococcenes allow the possibility of the continuous harvest of products. Thus, industrial mimickry of Nature's competitive advantage represents an improvement on systems suited to the production and harvest of renewable hydrocarbons. Botryococcenes are the natural product of choice as a starting material for a number of hydrocarbon based products, such as petrochemicals, pharmaceuticals, and fuels.

What is claimed is:

1. A method for the production of hydrocarbons which comprises cultivating species of the Chlorophyta in a nutrient medium having a phosphate content of at least about 348 ppm, a zinc content of at least about 0.2 ppm, and an iron content of at least about 3 ppm, harvesting the cultivated strain, and recovering therefrom said hydrocarbons.

2. The method of claim 1, wherein said species are selected from the Trebouxiophyceae.

3. The method of claim 1, wherein said species are selected from the group consisting of *Botryococcus* species and varieties and strains thereof.

4. The method of claim 1, wherein said cultivating step produces a biomass, and further comprising exposing said Chlorophyta to a second nutrient medium having a phosphate content of at least about 80 mM.

5. The method of claim 1, wherein said nutrient medium further comprises:
   200 ppm to 30,000 ppm N;
   100 ppm to 150,000 ppm $P_2O_5$; and
   100 ppm to 35000 ppm $K_2O$.

6. The method of claim 1, wherein said nutrient medium comprises nutrients selected from the group consisting of phosphate salts, ammonium salts, calcium salts, potassium salts, magnesium salts, sodium salts, phosphoric acid, pyrophosphates, polyphosphates, glycerophosphates and mixtures thereof.

7. The method of claim 4, wherein said second nutrient medium comprises from about 800 ppm to about 150,000 ppm phosphates and from about 5 ppm to about 70 ppm soluble zinc.

8. The method of claim 7, wherein said second nutrient medium further comprises nutrients selected from the group consisting of ammonium salts, potassium salts, magnesium salts, sodium salts, phosphoric acid, pyrophosphates, polyphosphates, glycerophosphates and mixtures thereof.

9. The method of claim 8, wherein said second nutrient medium further comprises phosphate buffers comprised of monobasic, dibasic, and tribasic salts; citrates; and Krebs Cycle carboxylates.

10. The method of claim 9, wherein said second nutrient medium comprises 25 ppm to 250 ppm soluble magnesium, 0.3 ppm to 3 ppm soluble manganese, 3 ppm to 10 ppm soluble iron, and 5 ppm to 70 ppm soluble zinc ($Zn^{+2}$).

11. The method of claim 1, wherein said hydrocarbons are cultivated on an aqueous solid substrate.

12. The method of claim 11, wherein said substrate is selected from the group consisting of paper, plastic, colloids, phycocolloids, agar, agarose, carrageenan, agar substitutes, textiles, gel, mud, soil, earth, shale, clays, foam, ceramics, concrete, brick, metal foam, wovens and nonwovens.

13. The method of claim 1, wherein said Chlorophytan is cultivated with a supply of carbon dioxide and carbonates.

14. The method of claim 1, wherein the said Chlorophytan is cultivated under light exposure of 100 to 2000 $\mu E/m^2/sec$ PAR illumination.

15. The method of claim 1, wherein said hydrocarbons comprise any of $C_nH_{2n-10}$, where n is from 30 to 37, inclusive.

16. The method of claim 1, wherein said zinc content is at least about 5 ppm.

17. The method of claim 1, wherein said nutrient medium further comprises at least 5 ppm soluble iron.

18. A method for the production of botryococcene hydrocarbons in a mud niche, comprising cultivating, in said mud niche, species of the Chlorophyta that accumulate botryococcene, in a nutrient medium having a phosphate content of at least about 348 ppm, a zinc content of at least about 0.2 ppm, and an iron content of at least about ppm, harvesting the cultivated strain, and recovering therefrom said hydrocarbons.

19. The method of claim 18, wherein said cultivating step produces a biomass, and further comprising exposing said Chlorophyta to a second nutrient medium having a phosphate content of at least about 80 mM.

20. The method of claim 19, wherein said Chlorophyta is exposed to said second nutrient medium by spraying said second nutrient medium.

21. The method of claim 1, further comprising exposing said Chlorophyta to a second nutrient medium having a $Ca^{+2}$ of 1 ppm.

22. The method of claim 1, further comprising exposing said Chlorophyta to a second nutrient medium having a $MgSO_4$ content of 1 ppm.

* * * * *